United States Patent [19]
Iizuka et al.

[11] Patent Number: 4,656,269
[45] Date of Patent: Apr. 7, 1987

[54] HISTIDINE DERIVATIVES

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd., Nagano, Japan

[21] Appl. No.: 852,260

[22] Filed: Apr. 15, 1986

[30] Foreign Application Priority Data

Apr. 15, 1985 [JP] Japan .................................. 60-79726

[51] Int. Cl.$^4$ .................. C07D 233/64; C07D 413/12
[52] U.S. Cl. ................................... 544/139; 546/205; 548/336; 548/344
[58] Field of Search .................. 544/139; 546/205; 548/336, 344; 260/998.2

[56] References Cited

FOREIGN PATENT DOCUMENTS 188862 11/1983 Japan .

Primary Examiner—Robert W. Ramsuer
Attorney, Agent, or Firm—Sughrue, Mion, Zinn, Macpeak and Seas

[57] ABSTRACT

Novel amino acid derivatives useful as a therapeutic agent are disclosed. These amino acid derivatives and the pharmaceutically acceptable salts thereof have a human renin inhibitory effect when administered orally and are useful for treatment of hypertension, especially renin-associated hypertension.

17 Claims, No Drawings

HISTIDINE DERIVATIVES

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially renin-associated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contracts the vascular smooth muscle and acts on the adrenal cortex to secrete the aldosterone which regulates salts and water balance. Accordingly, the renin-angiotensin system plays an important role in hypertension. In fact, a specific inhibitor of angiotensin I converting enzyme has been investigated and developed as a practical medicament for hypertension. Thus, an effective inhibitor of renin has long been sought as an agent for treatment of hypertension, especially renin-associated hypertension. As a result, it has been found that certain peptides show a renin inhibitory effect, as described in Japanese Patent Application (OPI) Nos. 155345/84, 227851/84 and 110661/84, (The term "OPI" as used herein refers to an unexamined Japanese patent application); Japanese Patent Publication No. 39149/83, Biochemical and Biophysical Research Communications, Vol. 118, pages 929–933, 1984; and European Patent Application Nos. 77029($A_2$), 77028($A_2$) and 81783($A_b$ 2).

Of these prior art references, Japanese Patent Application (OPI) No. 155345/84 discloses peptides represented by the following formula:

A—(CH$_2$)$_{\overline{p}}$—B—(CH$_2$)$_{\overline{q}}$—CHCO—His—NHCHCHCH$_2$CO—F—G
                                                    |                    |
                                                    D                   CH$_2$—E
                                                                         |

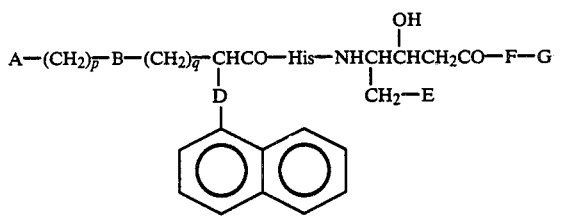

wherein A represents a hydrogen atom, a phenyl group or 10,11-dihydro-5H-dibenzo[a,d]cycloheptenyl group, B represents —O—, —CH=CH—, or —CH$_2$—, p and q, which may be the same or different, each represents an integer of from 0 to 3, D represents a hydrogen atom, a lower alkyl group, a lower alkenyl group, a phenyl group or a phenylalkyl group, E represents a phenyl group, a cyclohexyl group or an isopropyl group, His represents an L-histidyl group, F represents a residual group of an amino acid such as an L-leucyl, an L-isoleucyl, an L-leucyl-L-phenylalanyl, an L-phenylalanyl-L-phenylalanyl and an L-alanyl-L-phenylalanyl group, and G represents a protective group attached to the terminal carbon atom of an amino acid, such as an amino group, an alkylamino group, an arylalkylamino group and an alkoxy group.

Japanese Patent Application (OPI) No. 227851/84 also discloses peptides represented by the following formula:

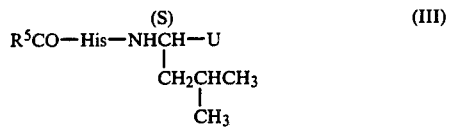

(III)

wherein R$^5$CO— represents an aliphatic acyl group, an aromatic acyl group, an aromatic aliphatic acyl group, a heterocyclic acyl group or a heterocyclic aliphatic acyl group, said acyl groups may be sustituted with an amino, a protected amino, a hydroxy, a substituted dithio, an alkyl, an alkoxy, an alkoxycarbonyl, or a nitro group or a halogen atom, U represents a formyl group, or

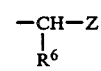

wherein R$^6$ represents a hydrogen atom, an alkyl group, an alkyl group having a hydroxy, a mercapto, an amino, a carbamoyl, a formyl, an aromatic ring or a heterocyclic ring substituent, Z represents a hydroxy, mercapto or formyl group, or U represents

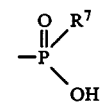

wherein R$^7$ represents a hydroxy group or an alkyl group having a hydroxy, a mercapto, an amino, a carbamoyl, or a formyl group, or an aromatic ring or a heterocyclic ring substituent, His represents an L-histidyl group, C$^{(S)}$ represents a carbon atom in the S-configuration, provided that, when U represents a formyl group, R$^5$CO— does not represent a benzyloxy-carbonyl-L-phenylalanyl group or a benzyloxycarbonyl-L-prolyl-L-phenylalanyl group.

The noted Biochemical and Biophysical Research Communications article discloses a peptide represented by the formula:

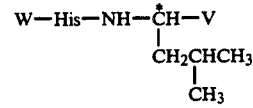

wherein W represents a benzyloxycarbonyl group, an N-benzyloxycarbonyl-L-phenylalanyl group or an N-benzyl-oxycarbonyl-3-(1-naphthyl)-L-alanyl group, V represents a formyl group or a hydroxy group and C* represents a carbon atom in the L-configuration.

Japanese Patent Publication No. 39149/83 discloses peptides represented by the following formula:

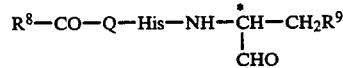

wherein R$^8$ represents a methyl group, an ethyl group, a benzyl group, an adamantyl group or a benzyloxy group, Q represents an L-phenylalanyl group, an L-prolyl-L-phenylalanyl group or an L-histidyl-L-prolyl-L-phenylalanyl group, His represents an L-histidyl group, $R^9$ represents an isopropyl group, and C* represents a carbon atom in the L-configuration. These peptides show a renin inhibitory effect, however, they are easily hydrolyzed by proteolytic enzymes of the gastorointestinal tract such as chymotrypsins. Therefore, these peptides have a drawback that their renin inhibitory effect can not be expected when they are administered orally.

On the other hand, the peptides disclosed in the above European Patent Applications are polypeptides and have difficulties in their preparation and purification. Furthermore, they lose their pharmacological effects when administered orally similar to the peptides disclosed in the Japanese Patent Publication No. 39149/83, and their utility is thus limited.

Thus, development of renin inhibitors which can display a sufficient therapeutic effect by oral administration has long been desired.

SUMMARY OF THE INVENTION

Accordingly, an object of this invention is to provide new amino acid derivatives which exhibit a specific renin inhibitory effect when administered orally to mammalia including humans.

Another object of this invention is to provide new amino acid derivatives and pharmaceutically acceptable salts thereof.

A further object of this invention is to provide pharmaceutical compositions comprising dipeptides or pharmaceutically acceptable salts thereof.

A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

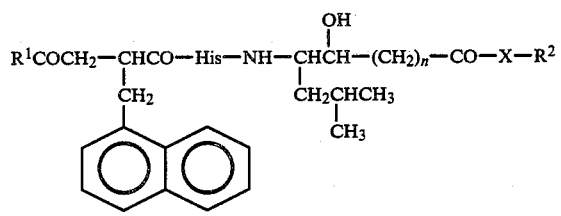

wherein $R^1$ represents a monoalkylamino group having 1 to 3 carbon atoms, a dialkylamino group having 2 to 6 carbon atoms, or

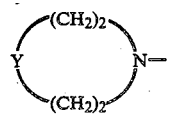

in which Y represents a chemical bond, an oxygen atom or a methylene group, His represents an L-histidyl group, n represents 0 or 1, X represents an oxygen atom or —NH—, $R^2$ represents a straight- or branched alkyl group having 1 to 7 carbon atoms; or a pharmaceutically acceptable salts thereof.

DETAILED DESCRIPTION OF THE INVENTION

These amino acid derivatives of formula (I) of the present invention and pharmaceutically acceptable salts thereof inhibit renin activity in a human reninsheep renin substrate system. Furthermore, the amino acid derivatives of the present invention are stable against proteolytic enzymes such as pepsin and chymotrypsins.

These findings demonstrate that the amino acid derivatives of formula (I) of the present invention exhibit a human renin inhibitory effect when administered orally to mammalia, including humans, and thus are useful for treatment of hypertension, especially renin-associated hypertension.

The amino acid derivatives of formula (I) of the present invention can be prepared according to well known method. That is, the amino acid derivatives of the present invention represented by formula (I):

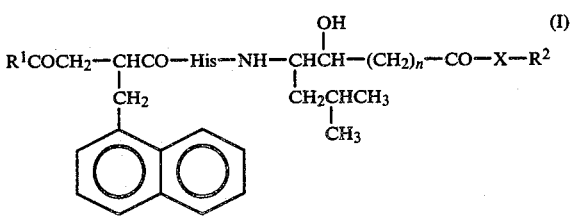

wherein $R^1$, His, n, X and $R^2$ have the same meanings as defined above, can be prepared by reacting a compound represented by formula:

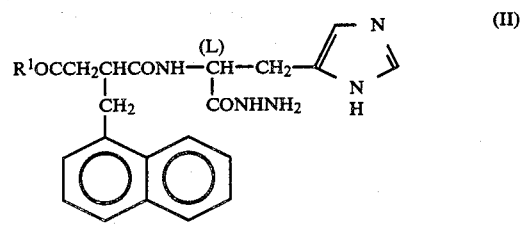

wherein $C^{(L)}$ means a carbon atom in the L-configuration, and $R^1$ has the same meaning as defined above, with a compound represented by formula:

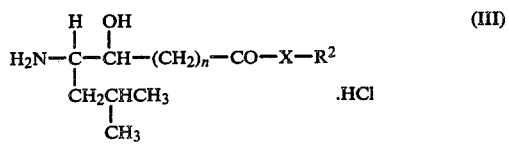

wherein n, X and $R^2$ have the same meanings as defined above.

The compounds of formula (II) used as a starting material can be prepared by reacting a reactive functional derivative of an acid compound of formula:

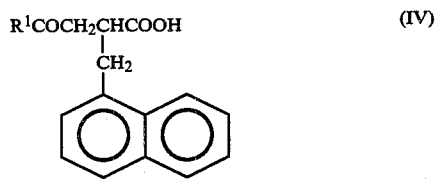

wherein R¹ has the same meaning as defined above, with L-histidine methyl ester dihydrochloride in N,N-dimethylformamide to obtain a compound represented by formula:

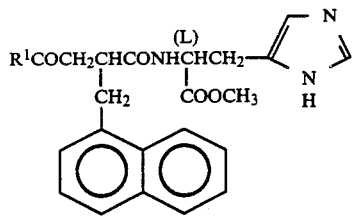
(V)

wherein R¹ and C$^{(L)}$ have the same meanings as defined above, and reacting the resulting compound with hydrazine monohydrate in methanol.

The acid compounds represented by formula (II) above can be prepared by the method described below or an analogous method thereof. That is, the acid compounds represented by formula (II) can be prepared by reacting 1-naphthaldehyde with diethyl succinate to obtain the compound represented by the formula:

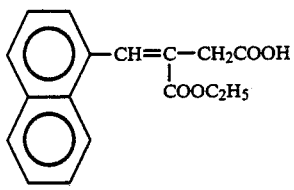
(VI)

hydrolyzing the resulting compound to obtain the corresponding dicarboxylic acid, dehydrating the dicarboxylic acid compound obtained in acetic anhydride to obtain an succinic anhydride compound represented by formula:

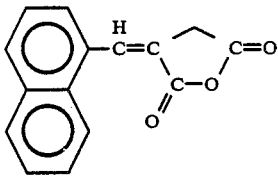
(VII)

reacting the succinic anhydride compound with an amine to obtain a compound represented by formula:

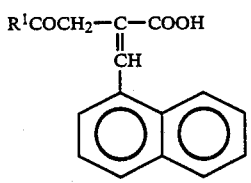
(VIII)

wherein R¹ has the same meaning as defined above, and then hydrogenating the resulting compound over palladium charcoal.

Alternatively, the acid compound represented by formula (II) can be prepared by hydrogenating a compound represented by formula (VI) to obtain a compound represented by formula (IX):

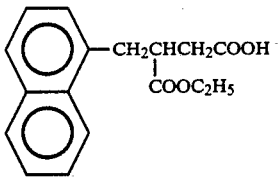
(IX)

then reacting the resulting compound with an amine using carbonyldiimidazole, and hydrolyzing a compound obtained with sodium hydroxide.

The compounds represented by formula (III) used as starting material can be prepared by methods described in literature or an analogous method thereof. That is, the compound wherein n is 0 can be prepared by esterifing or amidating 3-amino-2-hydroxy-5-methylhaxanoic acid which is prepared according to the method described in J. Org. Chem., Vol. 45, pages 2288-2290, 1980. The compound wherein n is 1 can be prepared by esterifing or amidating statine or N-(tert-butyloxycarbonyl)statine.

The reaction of a compound represented by formula (II) with a compound of formula (III) can be carried out according to the following manner.

That is, the amino acid derivative of formula (I) of the present invention can be prepared by suspending a compound of formula (II) in N,N-dimethylformamide, adding hydrogen chloride in a proportion of from about 3 to about 5 molar amounts per mole of the compound of formula (II) to the suspension, adding isoamyl nitrite in a proportion of from about 1 to about 3 molar amounts per mole of the compound of formula (II) to the mixture, reacting the mixture for about 5 to about 30 minutes at about $-20°$ to about $-5°$ C., adjusting a pH of the reaction mixture to about 8 to about 9 with triethylamine, adding dropwise the mixture to a solution of the compound of formula (III) and triethylamine in an equimolar amount to the compound of formula (II) in N,N-dimethylformamide under ice-cooling, preferably $-20°$ to $0°$ C., reacting the mixture for about 5 to about 20 hours at $0°$ C. or at room temperature, adding a 5% aqueous sodium bicarbonate solution and extracting with ethyl acetate, evaporating the ethyl acetate layer, and then purifying the residue by preparative silica gel thin layer chromatography or silica gel flash column chromatograpy.

The amino acid derivatives represented by formula (I) of the present invention can be converted according to conventional methods to a pharmaceutically acceptable salt thereof. Examples of such pharmaceutically acceptable salts include pharmaceutically acceptable inorganic or organic acid salts such as a hydrochloric acid salt, a sulfuric acid salt, a p-toluenesulfonic acid salt, an acetic acid salt, a citric acid salt, tartaric acid salt, a succinic acid salt, a fumaric acid salt and the like. These salts have a renin inhibitory effect as high as the corresponding compound having a free amino group and are stable against proteolytic enzyme, and thus they show the desired renin inhibitory effect even by oral administration.

The amino acid derivatives represented by formula (I) of the present invention possess a strong inhibitory effect on human renin, for example, the amino acid derivatives of formula (I) produce a 50% inhibition in renin-sheep substrate system and in human high renin plasma at $6.9 \times 10^{-7}$ to $2.2 \times 10^{-8}$ and $5.2 \times 10^{-6}$ to $5.4 \times 10^{-9}$ molar concentrations, respectively, and reduce blood pressure of marmoset in a high renin state with a low toxicity, and thus are useful as a therapeutically active agent for treatment of hypertension, especially renin-associated hypertension.

The amino acid derivatives represented by formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salts of the formula (I) of the present invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of the present invention may be in a range of from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following examples and reference examples. The melting point of the product obtained was uncorrected. The NMR spectra of the products were measured by JEOL's High Resolution NMR Spectrometer Type JNM-GX 270. The Mass spectra of the products were measured by JEOL's Mass Spectromer Type JMS-DX 300 according to the FAB method. Thin layer chromatography was carried out using Merck's pre-coated plates silica gel 60 $F_{254}$ and column chromatography was carried out by employing Merck's Kiesel gel 60 (230-440 mesh). Thin layer chromatography was carried out by using a lower layer of a mixture of chloroform, methanol and water in a proportion of 8/3/1 (by volume) (mixture A) and a mixture of chloroform and methanol in a proportion of 5/1 (by volume) (mixture B) as eluents, and an $Rf_1$ (mixture A) value and $Rf_2$ (mixture B) value were calculated.

REFERENCE EXAMPLE 1

2-(1-Naphthylmethyl)-3-(morpholinocarbonyl)-propionic acid

To a solution of 32.3 g of diethyl succinate and 29.0 g of 1-naphthaldehyde in 100 ml of absolute ethanol was added 10.7 g of sodium hydride (50% dispersion in mineral oil) under ice-cooling, and then the mixture was heated under reflux for 0.5 hours. To the reaction was added 230 ml of 1N-aqueous sodium hydroxide solution, and the mixture was heated under reflux for 1 hour. The reaction mixture was evaporated under reduced pressure, and water was added to the residue. The mixture was extracted with diethyl ether to remove neutral substances. The aqueous layer was acidified by adding concentrated hydrochloric acid, and extracted with diethyl ether. The ethereal layer was washed a saturated sodium chloride aqueous solution, dried over anhydrous magnesium sulfate, and evaporated under reduced pressure. Benzene was added to the residue, and the precipitated crystals were collected by flitration to obtain 26.5 g of 2-(1-naphthylmethylene)succinic acid as yellow crystals.

A solution of 24.5 g of 2-(1-naphthylmethylene)succinic acid in 260 ml of acetic anhydride was heated at 60° C. for 1 hour, and the reaction mixture was evaporated under reduced pressure. A mixture of benzene and hexane (1:1) was added to the residue, and the precipitated crystals were collected by filtration to obtain 16.0 g of 2-(1-naphthylmethyl)succinic anhydride as orange yellow crystals.

A solution of 1.00 g of 2-(1-naphthylmethylene)succinic anhydride and 0.37 g of morpholine in 31 ml of dry dichloromethane was stirred for 2 hours at room temperature. The reaction mixture was evaporated under reduced pressure, and the residue was crystallized from a mixture of ethyl acetate, benzene and hexane (1:1:1) to obtain 1.10 g of 2-(1-naphthylmethylene)-3-(morpholinocarbonyl)propionic acid as colorless crystals. A solution of 1.00 g of the propionic acid compound was hydrogenated over 0.1 g of a 10% palladium charcoal under a hydrogen atmosphere. After filtration of the catalyst, the filtrate was evaporated under reduced pressure. The residue was crystallized from hexane to give 0.90 g of 2-(1-naphthylmethyl)-3(morpholinocarbonyl)propionic acid as a white powder.

$Rf_1$: 0.67.
MS: MH+, 328.
Melting point: 64°-68° C.
IR (KBr): $\nu_{CO}$ 1720, 1640 cm$^{-1}$.
NMR (CDCl$_3$): δ2.37-2.70 (m, 2H), 3.08-3.8 (m, 11H), 7.27-8.16 (m, 7H).

REFERENCE EXAMPLE 2

2-(1-Naphthylmethyl)-3-(morpholinocarbonyl)propionic acid

To a solution of 17.40 g of diethyl succinate and 15.62 g of 1-naphthaldehyde in 100 ml of absolute ethanol was added 6.00 g of sodium hydride (50% dispersion in mineral oil) under ice-cooling, and the mixture was heated under reflux for 3 hours. The reaction mixture was evaporated under reduced pressure, and water was added to the residue. The mixture was extracted with diethyl ether to remove neutral materials. The aqueous layer was acidifed with concentrated hydrochloric acid, and then extracted with diethyl ether. The ethereal layer was washed with a saturated sodium chloride aqueous solution, dried over anhydrous magnesium sulfate, and evaporated under reduced pressure to give 23.60 g of 3-ethoxycarbonyl-4-(1-naphthyl)-3-butenoic acid as a yellow oil. A solution of 1.39 g of the butenoic acid in 50 ml of acetic acid was hydrogenated over 700 mg of a 10% palladium charcoal under a hydrogen atmosphere. After filtration of the catalyst, the filtrate was evaporated under reduced pressure to give 1.04 g of 3-ethoxycarbonyl-4(1-naphthyl)butyric acid as a brawn oil. To a solution of 1.03 g of the butyric acid in 20 ml of dry dichloromethane was added 0.64 g of 1,1'-carbonyldiimidazole, and the mixture was stirred for 1 hour at room temperature. Then, to the reaction mixture was added 0.35 g of morpholine, and the mixture was stirred for 15 hours. The reaction mixture was evaporated under reduced pressure, and 0.5% aqueous sodium bicarbonate solution was added to the residue. The mixture was extracted with ethyl acetate, and the ethyl acetate layer was washed succesively with water, dilute hydrochlorid acid and water, dried over anhydrous magnesium sulfate, and evaporated under reduced pressure. The residue was purified by silica gel flash column chromatography (eluent: benzene/ethyl acetate=4/1 by volume) to obtain 0.86 g of ethyl 2-(1-naphthylmethyl)-3-(morpholinocarbonyl)propionate as a colorless oil. The mixture of 0.84 g of the ester compound, 3 ml of a 2N-aqueous sodium hydroxide solution and 5 ml of ethanol was stirred for 16 hours at room temperature. The reaction mixture was evaporated under reduced pressure, and water was added to the reaction mixture. The mixture was extracted with diethyl ether to remove neutral materials. The aqueous layer was acidified by adding concentrated hydrochloric acid, and extracted with diethyl ether. The ethereal layer was washed with a saturated sodium chloride aqueous solution, dried over anhydrous magnesium sulfate, and evaporated under reduced pressure to give 0.69 g of 2-(1-naphthylmethyl)-3-(morpholinocarbonyl)propionic acid as a white powder. The chemical properties, $Rf_1$, MS, Melting point, IR and NMR, of the carboxylic acid obtained were identical with those of the carboxylic acid compound obtained by Reference Example

REFERENCE EXAMPLE 3

In a manner similar to Reference Example 1, the following carboxylic acid compounds were obtained.

2-(1-Naphthylmethyl)-3-(piperidinocarbonyl)propionic acid $Rf_1$: 0.72.
MS: MH+326.
Melting point: 43°–47° C.
IR (KBr): $\nu$co 1720, 1595 cm$^{-1}$.
NMR (CDCl$_3$): δ0.95–1.70 (m, 6H), 2.50–3.85 (m, 9H), 7.3–8.15 (m, 7H).

2-(1-Naphthylmethyl)-3-(pyrolidinocarbonyl)propionic acid $Rf_1$: 0.64.
MS: MH+, 312.
Melting point: below 30° C.
IR (KBr): $\nu$co 1720, 1600 cm$^{-1}$.
NMR (CDCl$_3$): δ: 1.79(t, 4H, J=3.3 Hz), 2.4–2.6 (m, 2H), 2.8–3.9 (m, 7H), 7.2–8.2 (m, 7H)

2-(1-Naphthylmethyl)-3-(dimethylcarbamoyl)propionic acid $Rf_1$: 0.71.
MS: MH$^{30}$, 501.
Melting point: 46°–48° C.
IR (KBr): $\nu$co 1720, 1640 cm$^{-1}$.
NMR (CDCl$_3$): δ: 2.4–3.4 (m, 10H), 3.80 (dd, 1H, J=3.8, 13.7 Hz), 7.2–8.15(m, 7H).

2-(1-Naphthylmethyl)-3-(ethylcarbamoyl)propionic acid $Rf_1$: 0.66.
MS: MH+, 286.
Melting point: 45°–50° C.
IR (KBr): $\nu$co 1700, 1610 cm$^{-1}$.
NMR (CDCl$_3$): δ: 1.08(t,3H, J=7.1 Hz), 2.3–2.55 (m, 2H), 2.7–3.8(m, 5H), 5.51(s, 1H), 7.25–8.1(m, 7H).

REFERENCE EXAMPLE 4

N-[2-(1-Naphthylmethyl)-3-(morpholinocarbonyl)propionyl]-L-histidine hydrazide

To a suspension of 0.89 g of 2-(1-naphthylmethyl)-3-(morpholinocarbonyl)propionic acid and 0.79 g of L-histidine methyl ester dihydrochloride in 23 ml of N,N-dimethylformamide were added successively 0.70 ml of diphenylphosphoryl azide and 1.5 ml of triethylamine under ice-cooling, and the mixture was stirred for 16 hours under ice-cooling. The reaction mixture was evaporated under reduced pressure, and a 5% aqueous sodium bicarbonate solution was added to the residue. The mixture was extracted with ethyl acetate, and then the ethyl acetate layer was washed with water, dried over anhydrous magnesium sulfate, and evaporated under reduced pressure. Diethyl ether was added to the residue, and precipitated crystals were collected by filtration to give 1.25 g of N-[2-(1-naphthylmethyl)-3-(morpholinocarbonyl)propionyl]-Lhistidine methyl ester as a white powder. To a solution of 0.98 g of the ester compound in 10 ml of methanol was added 0.52 g of hydrazine monohydrate, and the mixture was stirred for 4 hours at room temperature. The reaction mixture was evaporated under reduced pressure. The residue was separated by silica gel flash column chromatography (eluent: chloroform/methanol=10/1), and fraction containing desired product which has $Rf_1$ value of 0.49 was combined to obtain 0.23 g of N-[2-(1-naphthylmethyl)-3-(morpholinocarbonyl)propionyl]-L-histidine hydrazide as a white powder.

Melting point: 115°–119° C.
$Rf_1$: 0.49.
MS: MH+, 479.
IR (KBr): $\nu$co 1620 cm$^{-1}$.

REFERENCE EXAMPLE 5

In a manner similar to Reference Example 4, the following hydrazide compounds were obtained.

N-[2-(1-Naphthylmethyl)-3-(piperidinocarbonyl)propionyl]-L-histidine hydrazide $Rf_1$: 0.53, 0.59.
MS: MH+, 477.
Melting point: 90°–97° C.
IR (KBr): $\nu$co 1615 cm$^{-1}$.

N-[2-(1-Naphthylmethyl)-3-(pyrolidinocarbonyl)propionyl]-L-histidine hydrazide $Rf_1$: 0.59.
MS: MH+, 463.
Melting point: 79°–84° C.
IR (KBr): $\nu co$ 1610 cm$^{-1}$.

N-[2-(1-Naphthylmethyl)-3-(dimethylcarbamoyl)propionyl]-L-histidine hydrazide $Rf_1$: 0.38, 0.44.
MS: MH+, 501.
Melting point: 78° C. (decomposition).
IR (KBr): $\nu co$ 1620 cm$^{-1}$.

N-[2-(1-Naphthylmethyl)-3-(ethylcarbamoyl)propionyl]-L-histidine hydrazide $Rf_1$: 0.36, 0.41.
MS: MH+, 437.
Melting point: 154°–161° C.
IR (KBr): $\nu co$ 1625 cm$^{-1}$.

REFERENCE EXAMPLE 6

(2RS, 3S)-3-Amino-2-hydroxy-5-methylhexanoic acid

A solution containing 3.43 g of sodium hydrogen sulfite in 20 ml of water was added to 2.81 g of N-carbobenzoxy-L-leucinal, and the mixture was stirred for 14 hours under ice-cooling. A solution of 1.41 g of potassium cyanide in 50 ml of water and 200 ml of ethyl acetate were added to the reaction mixture, and the mixture was stirred for 4 hours at room temperature. The ethyl acetate layer was washed with a saturated sodium chloride aqueous solution, dried over anhydrous magnesium sulfate, and evaporated under reduced pressure to give 2.54 g of 3-carbobenzoxyamino-2-hydroxy-5-methylhexanenitrile as a colorless oil. A mixture of 20 ml of dioxane and 20 ml of concentrated hydrochloric acid was added to 500 mg of the nitrile, and the mixture was heated under reflux for 12 hours. The reaction mixture was evaporated under reduced pressure, and the residual crystals were purified by cation exchange column chromatography (eluent: a 2N aqueous NH$_4$OH solution) to obtain 254 mg of (2RS, 3S)-3-amino-2-hydroxy-5-methylhexanoic acid as colorless crystals (a mixture in ratio of 2R and 2S being about 7:3).

Melting point: 137°–140° C.
IR (KBr): $\nu co$ 1570 cm$^{-1}$.
NMR (D$_2$O): δ: 0.8–1.0(m, 6H), 1.2–1.4(m, 2H), 1.55–1.8(m, 1H), 3.0–3.4(m, 1H), 3.89(d, 0.7H, J=3.3 Hz), 4.00(d, 0.3H, J=3.3 Hz).
MS: MH+, 162.

REFERENCE EXAMPLE 7

Methyl (2RS, 3S)-3-amino-2-hydroxy-5-methylhexanoate hydrochloride

Hydrogen chloride was passed into a solution 110 mg of (2RS, 3S)-3-amino-2-hydroxy-5-methylhexanoic acid in 10 ml of methanol under ice-cooling, and the mixture was stirred overnight. The reaction mixture was evaporated to dryness under reduced pressure to obtain 150 mg of methyl (2RS, 3S)-3-amino-2-hydroxy-5-methylhexanoate hydrochloride as a white powder.

IR (KBr): $\nu co$ 1740 cm$^{-1}$.
NMR (D$_2$O): δ: 0.85–1.0(m, 6H), 1.4–1.9(m, 3H), 3.65–3.8(m, 1H), 3.83(s, 3H), 4.45–4.7(m, 1H).

REFERENCE EXAMPLE 8

(2RS, 3S)-3-tert-Butyloxycarbonylamino-2-hydroxy-5-methylhexanoic acid

To a solution of 3.22 g of (2RS, 3S)-3-amino-2-hydroxy-5-methylhexanoic acid and 3.08 ml of triethylamine in 30 ml of water was added a solution of 5.41 g of 2-(tert-butyloxycarbonyloxyimino)-2-phenylacetonitrile in 30 ml of dioxane, and the mixture was stirred ofr 16 hours at room temperature. To the reaction mixture was added 100 ml of water, and the mixture was extracted with ethyl acetate to remove neutral material. The aqueous layer was acidified with an aqueous citric acid solution and extracted with ethyl acetate. The ethyl acetate layer was washed with a saturated sodium chloride solution, dried over anhydrous magnesium sulfate, and evaporated under reduced pressure to obtain 5.10 g of (2RS, 3S)-3-tert-butyloxycarbonylamino-2-hydroxy-5-methylhexanoic acid as a pale yellow oil.

IR (neat): $\nu co$ 1710, 1675 cm$^{-1}$.
NMR (CDCl$_3$): δ: 0.8–1.0(m, 6H), 1.2–1.85(m, 12H), 3.95–4.4(m, 2H), 4.8–5.0(br, 1H), 9.4–10.4(br, 1H).

REFERENCE EXAMPLE 9

Isopropyl (2RS, 3S)-3-amino-2-hydroxy-5-methylhexanoate hydrochloride

Hydrogen chloride was passed into a solution of 4.0 g of (2RS, 3S)-3-amino-2-hydroxy-5-methylhexanoic acid in 50 ml of isopropyl alcohol with stirring under ice-cooling, and then 100 ml of dry benzene was added to the reaction mixture, and the mixture was heated under reflux for 10 minutes while removing water formed during the reaction using a molecular sieve. The reaction mixture was evaporated to dryness under reduced pressure to obtain 5.7 g of isopropyl (2RS, 3S)-3-amino-2-hydroxy-5-methylhexanoate hydrochloride as a white powder.

IR (KBr): $\nu co$ 1725 cm$^{-1}$.
NMR (D$_2$O): δ: 0.8–1.1(m, 6H), 1.29(d, 6H, J=6.6 Hz), 1.5–2.0(m, 3H), 3.6–3.75(m, 1H), 4.3–4.7(m, 1H), 5.0–5.2(m, 1H).

EXAMPLE 1

Isopropyl (2RS, 3S)-3-{N-[2-(1-naphthylmethyl)-3-(morpholinocarbonyl)propionyl]-L-histidyl}amino-2-hydroxy-5-methylhexanoate To a solution of 50 mg of N-[2-(1-naphthylmethyl)-3-morpholinocarbonyl)propionyl]-L-histidine hydrazide in 1 ml of N,N-dimethylformamide were added successively 0.068 ml of a dry 5.1N-hydrogen chloride in N,N-dimethylformamide solution and 0.017 ml of isoamyl nitrite at −20° C. with stirring. After disappearance of hydrazide compound, the reaction mixture was cooled to −30° C., and the reaction mixture was neutralized by adding 0.048 ml of triethylamine to prepare a solution of N-[2-(1-naphthylmethyl)-3-(morpholinocarbonyl)propionyl]-L-histidine azide. The cold azide solution was added dropwise to a solution of 25 mg of isopropyl (2RS, 3S)-3-amino-2-hydroxy-5-methylhexanoate hydrochloride and 0.032 ml of triethylamine in 2 ml of N,N-dimethylformamide under ice-cooling, and the mixture was stirred for 16 hours. A 5% aqueous sodium bicarbonate solution was added to the reaction mixture, and the mixture was extracted with ethyl acetate, washed with a saturated sodium chloride, dried over anhydrous magnesium sulfate, and evaporated under reduced pressure. The residue was purified by preparative silica gel thin layer chromatography (developing solvent: chloroform/methanol=5/1 by volume $Rf_2=0.53$ to obtain 4 mg of isopropyl (2RS, 3S)-3-{N-[2-(1-naphthylmethyl)-3-(morpholinocarbonyl)propionyl]-L-histidyl}amino-2-hydroxy-5-methylhexanoate as a white powder.

Melting point: 95°–98° C.
$Rf_1$: 0.59.
$Rf_2$: 0.53.
MS: MH+, 650.

EXAMPLE 2

Methyl (2RS, 3S)-3-{N-[2-(1-naphthylmethyl)-3-(morpholinocarbonyl)propionyl]-L-histidyl}amino-2-hydroxy-5-methylhexanoate To a solution containing 102 mg of N-[2-(1-naphthylmethyl)-3-(morpholinocarbonyl)propionyl]-L-histidine hydrazide in 6 ml of N,N-dimethylformamide was added successively 0.13 ml of a dry 5.1N-hydrogen chloride in N,N-dimethylformamide solution and 0.04 ml of isoamyl nitrite at −20° C. with stirring. After disappearance of hydrazide compound, the reaction mixture was cooled to −30° C., and then the reaction mixture was neutralized by adding 0.10 ml of triethylamine to prepare a solution of N-[2-(1-naphthylmethyl)-3-(morpholinocarbonyl)propionyl]-L-histidine azide. The cold azide solution was added dropwise to a solution of 47 mg of methyl (2RS, 3S)-3-amino-2-hydroxy-5-methylhexanoate hydrochloride and 0.10 ml of triethylamine in 3.4 ml of N,N-dimethylformamide under ice-cooling, and the mixture was stirred for 16 hours. A 5% aqueous sodium bicarbonate solution was added to the reaction mixture, and the mixture was extracted with ethyl acetate. The ethyl acetate layer was washed with a saturated sodium chloride, dried over anhydrous magnesium sulfate, and evaporated under reduced pressure. The residue was separated by silica gel flash column chromatography (eluent: chloroform/methanol=15/1 by volume), and fraction containing desired product which has $Rf_1$ value of 0.59 was isolated to obtained 24 mg of methyl (2RS, 3S)-3-{N-[2-(1-naphthylmethyl)-3-(morpholinocarbonyl)propionyl]- -L-histidyl}amino-2-hydroxy-5-methylhexanoate as a white powder.

Melting point: 108°–113° C.
$Rf_1$: 0.59.
$Rf_2$: 0.52.
MS: MH+, 714.

EXAMPLE 3

(2RS, 3S)-3-{N-[2-(1-Naphthylmethyl)-3-(morpholinocarbonyl)propionyl]-L-histidyl}amino-2-hydroxy-5-methylhexanoylmethylamide To a solution of 261 mg of (2RS, 3S)-3-tert-butyloxycarbonylamino-2-hydroxy-5-methylhexanoic acid, 0.12 ml of a 30% aqueous trimethylamine solution, and 176 mg of 1-hydroxybenzotriazole in 2 ml of N,N-dimethylformamide and 2 ml of tetrahydrofuran was added 206 mg of dicyclohexylcarbodiimide under ice-cooling with stirring, and the mixture was stirred for 16 hours. The reaction mixture was cooled under ice-cooling, and insoluble materials were filtered off. The filtrate was evaporated under reduced pressure. The residue was dissolved in ethyl acetate, and the solution was washed successively with an aqueous citric acid solution, a 5% aqueous sodium bicarbonate solution and a saturated sodium chloride aqueous solution, dried over anhydrous magnesium sulfate, and evaporated under reduced pressure to obtain 267 mg of (2RS, 3S)-3-tert-butyloxycarbonylamino-2-hydroxy-5-methylhexanoylmethylamide as a white powder. [IR (KBr): $\nu$co 1690, 1625 cm$^{-1}$].

To a solution of 260 mg of the amide compound in 5 ml of methanol was added 2 ml of a 2N-hydrochloric acid, and the mixture was stirred for 16 hours at room temperature. The reaction mixture was evaporated under reduced pressure to obtain 189 mg of (2RS, 3S)-3-amino-2-hydroxy-5-methylhexanoylmethylamide hydrochloride as a white powder. [IR (KBr): $\nu$co 1650 cm$^{-1}$].

To a suspension of 130 mg of N-[2-(1-naphthylmethyl)3-(morpholinocarbonyl)propionyl]-L-histidine hydrazide in 2 ml of dry N,N-dimethylformamide were added successively 0.18 ml of a dry 5.1N-hydrogen chloride in dimethylformamide solution and 0.044 ml of isoamyl nitrite at −20° C. with stirring. After disappearance of hydrazide compound, the reaction mixture was cooled to −30° C., and neutralized with 0.12 ml of triethylamine to prepare a solution of N-[2-(1-naphthylmethyl)-3-(morpholinocarbonyl)propionyl]-L-histidine azide. The cold azide solution was added to a solution of 60 mg of (2RS, 3S)-3-amino-2-hydroxy-5-methylhexanoylmethylamide hydrochloride and 0.039 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride, dried over anhydrous magneisum sulfate, and evaporated under reduced pressure. The residue was purified by preparative silica gel thin layer chromatography (developing solvent: chloroform/methanol=5/1, $Rf_2=0.32$) to obtain 22 mg of (2RS, 3S)-3-{N-[2-(1-naphthylmethyl)-3-(morpholinocarbonyl)propionyl]-L-histidyl}amino-2-hydroxy-5-methylhexanoylmethylamide as a white powder.

Melting point: 123°–128° C.
$Rf_1$: 0.47.
$Rf_2$: 0.32.
MS: MH+, 621.

EXAMPLE 4

(2RS, 3S)-3-{N-[2-(1-Naphthylmethyl)-3-(morpholinocarbonyl)propionyl]-L-histidyl}amino-2-hydroxy-5-methylhexanoylisopropylamide To a solution of 430 mg of (2RS, 3S)-3-tert-butyloxycarbonylamino-2-hydroxy-5-methylhexanoic acid, 0.33 ml of isopropylamine, and 451 mg of 1-hydroxybenzotriazole in 2 ml of N,N-dimethylformamide and 2 ml of tetrahydrofuran was added 418 mg of dicyclohexylcarbodiimide under ice-cooling with stirring, and the mixture was stirred for 16 hours. The reaction mixture was cooled under ice-cooling, and insoluble materials were filtered off. The filtrate was evaporated under reduced pressure, and the residue was dissolved in ethyl acetate. The mixture was washed successively with an aqueous citric acid solution, a 5% aqueous sodium bicarbonate solution and a saturated sodium chloride aqueous solution, dried over anhydrous magnesium sulfate, and evaporated under reduced pressure to obtain 428 mg of (2RS, 3S)-3-tert-butyloxycarbonylamino-2-hydroxy-5-methylhexanoylisopropylamide as a yellow oil [IR (neat): $\nu$co 1685, 1630 cm$^{-1}$].

To a solution of 420 mg of the amide compound obtained in 10 ml of methanol was added 4 ml of a 2N-hydrochloric acid, and the mixture was stirred for 16 hours at room temperature. The reaction mixture was evaporated under reduced pressure to obtain 171 mg of (2RS, 3S)-3-amino-2-hydroxy-5-methylhexanoylisopropylamide hydrochloride as a white powder. [IR (KBr): $\nu$co 1640 cm$^{-1}$].

To a suspension of 160 mg of N-[2-(1-naphthylmethyl)-b 3-(morpholinocarbonyl)propionyl]-L-histidine hydrazide in 2 ml of dry N,N-dimethylformamide were added successively 0.21 ml of a dry 5.1N-hydrogen chloride in N,N-dimethylformamide and 0.054 ml of isoamyl nitrite at −20° C. with stirring. After disappearance of hydrazide compound, the reaction mixture was cooled to −30° C., and neutralized with 0.15 ml of triethylamine to prepare a solution of N-[2-(1-naphthylmethyl)-3-(morpholinocarbonyl)propionyl]-L-histidine azide. The cold azide solution was added dropwise to a solution of 80 mg of (2RS, 3S)-3-amino-2-hydroxy-5-methylhexanoylisopropylamide hydrochloride and 0.047 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methanol=5/1, Rf$_1$=0.47) to obtain 47 mg of (2RS, 3S)-3-{N-[2-(1-naphthylmethyl)-3-(morpholinocarbonyl)propionyl]-L-histidyl}amino-2-hydroxy-5-methylhexanoylisopropylamide as a white powder.

Melting point: 108°–113° C.
Rf$_1$: 0.67.
RF$_2$: 0.47.
MS: MH+, 649.

EXAMPLE 5

Isopropyl (2RS, 3S)-3-{N-[2-(1-Naphthylmethyl)-3-(piperidinocarbonyl)propionyl]-L-histidyl}amino-2-hydroxy-5-methylhexanoate To a suspension of 240 mg of N-[2-(1-naphthylmethyl)-3-(piperidinocarbonyl)propionyl]-L-histidine hydrazide in 3 ml of dry N,N-dimethylformamide were added successively 0.32 ml of a dry 5.1N-hydrogen chloride in N,N-dimethylformamide solution and 0.08 ml of isoamyl nitrite at −20° C. with stirring. After disappearance of hydrazide compound, the reaction mixture was cooled to −30° C. and neutralized with 0.23 ml of triethylamine to prepare a solution of N-[2-(1-naphthylmethyl)-3-(piperidinocarbonyl)propionyl]-L-histidine azide. The cold azide solution was added dropwise to a solution of 120 mg of isopropyl (2RS, 3S)-3-amino-2-hydroxy-5-methylhexanoate hydrochloride and 0.07 ml of triethylamine in 2 ml of dry N,N-dimethylformamide under ice-cooling with stirring, and the mixture was stirred for 16 hours. The reaction mixture was evaporated under reduced pressure. A 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was separated by silica gel flash column chromatography (eluent: chloroform/methanol=20/1 by volume), and fraction containing desired product which has Rf$_1$ value of 0.63 was combined and purified to obtain 18 mg of isopropyl (2RS, 3S)-3-{N-[2-(1-naphthylmethyl)-3-(piperidinocarbonyl)propionyl]-L-histidyl}amino-2-hydroxy-5-methylhexanoate as a white powder.

Melting point: 91°–97° C.
Rf$_1$: 0.63.
Rf$_2$: 0.54.
MS: MH+, 648.

EXAMPLE 6

Methyl (2RS, 3S)-3-{N-[2-(1-naphthylmethyl)-3-(piperidinocarbonyl)propionyl]-L-histidyl}amino-2-hydroxy-5-methylhexanoate To a suspension of 200 mg of N-[2-(1-naphthylmethyl)-3-(piperidinocarbonyl)propionyl]-L-histidine hydrazide in 2 ml of dry N,N-dimethylformamide were added successively 0.26 ml of a dry 5.1N-hydrogen chloride in N,N-dimethylformamide solution and 0.066 ml of isoamyl nitrite with stirring at −20° C. After disappearance of hydrazide compound, the reaction mixture was cooled to −30° C. and neutralized with 0.19 ml of triethylamine to prepare a solution of N-[2-(1-naphthylmethyl)-3-(piperidinocarbonyl)propionyl]-L-histidine azide. The cold azide solution was added dropwise to a solution of 88 mg of methyl (2RS, 3S)-3-amino-2-hydroxy-5-methylhexanoate hydrochloride and 0.058 ml of triethylamine in 2 ml of dry N,N-dimethylformamide with stirring under ice-cooling, and then the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was separated by silica gel flash column chromatography (eluent: chloroform/methanol=20/1 by volume), and fractions containing desired product which has Rf$_1$ value of 0.54 were combined to obtain 141 mg of methyl (2RS, 3S)-3-{N-[2-(1-naphthylmethyl)-3-(piperidinocarbonyl)propionyl]-L-histidyl}amino-2-hydroxy-5-methylhexanoate as a white powder.

Melting point: 91°–97° C.
Rf$_1$: 0.54.
Rf$_2$: 0.44.
MS: MH+, 620.

EXAMPLE 7

(2RS, 3S)-3-{N-[2-(1-Naphthylmethyl)-3-(piperidinocarbonyl)propionyl]-L-histidyl}amino-2-hydroxy-5-methylhexanoylmethylamide To a solution of 261 mg of (2RS, 3S)-3-tert-butyloxycarbonylamino-2-hydroxy-5-methylhexanoic acid, 0.12 ml of a 30% aqueous methylamine solution, and 176 mg of 1-hydroxybenzotriazole in 2 ml of tetrahydrofuran and 2 ml of N,N-dimethylformamide was added 206 mg of dicyclohexylcarbodiimide with stirring under ice-cooling, and the mixture was stirred for 16 hours. The reaction mixture was cooled in an ice bath, and insoluble materials were filtered off. The filtrate was evaporated under reduced pressure, and the residue was dissolved in ethyl acetate. The ethyl acetate layer was washed successively with an aqueous citric acid solution, a 5% aqueous sodium bicarbonate solution and a saturated sodium chloride aqueous solution, dried over anhydrous magnesium sulfate, and evaporated under reduced pressure to obtain 267 mg of (2RS, 3S)-3-tert-butyloxycarbonylamino-2-hydroxy-5-methylhexanoylmethylamide as a white powder. [IR (KBr): $\nu$co 1690, 1625 cm$^{-1}$].

To a solution of 260 mg of the amide compound obtained in 5 ml of methanol was added 2 ml of a 2N-hydrochloric acid, and the mixture was stirred for 16 hours at room temperature. The reaction mixture was evaporated under reduced pressure to obtain 189 mg of (2RS, 3S)-3-amino-2-hydroxy-5-methylhexanoylmethylamide hydrochloride as a white powder. [IR (KBr): $\nu$co 1650 cm$^{-1}$].

To a suspension of 126 mg of N-[2-(1-naphthylmethyl)-3-(piperidinocarbonyl)propionyl]-L-histidine hydrazide in 2 ml of dry N,N-dimethylformamide were added successively 0.17 ml of a dry 5.1N-hydrogen chloride in N,N-dimethylformamide solution and 0.042 ml of isoamyl nitrite at −20° C. with stirring. After disappearance of hydrazide compound, the reaction mixture was cooled to −30° C., and neutralized with 0.12 ml of triethylamine to prepare a solution of N-[2-(1-naphthylmethyl)-3-(piperidinocarbonyl)propionyl]-L-histidine azide. The cold azide solution was added dropwise to a solution of 56 mg of (2RS, 3S)-3-amino-2-hydroxy-5-methylhexanoylmethylamide hydrochloride and 0.036 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was separated by silica gel flash column chromatography (eluent: chloroform/methanol=15/1 by volume), and fractins containing the desired product which has Rf$_1$ value of 0.51 was combined to obtain 50 mg of (2RS, 3S)-3-{N-[2-(1-naphthylmethyl)-3-(piperidinocarbonyl)propionyl]-L-histidyl}amino-2-hydroxy-5-methylhexanoylmethylamide as a white powder.

Melting point: 124°–130° C.
Rf$_1$: 0.51.
Rf$_2$: 0.41.
MS: MH+, 619.

EXAMPLE 8

Methyl (2RS, 3S)-3-{N-[2-(1-naphthylmethyl)-3-(pyrrolidinocarbonyl)propionyl]-L-histidyl}amino-2-hydroxy-5-methylhexanoate To a solution of 80 mg of N-[2-(1-naphthylmethyl)-3-(pyrrolidinocarbonyl)propionyl]-L-histidine hydrazide in 2 ml of N,N-dimethylformamide were added successively 0.12 ml of a dry 5.1N-hydrogen chloride in N,N-dimethylformamide solution and 0.028 ml of isoamyl nitrite at −20° C., and the mixture was stirred. After disappearance of hydrazide compound, the reaction mixture was cooled to −30° C. and neutralized with 0.078 ml of triethylamine to prepare a solution of N-[2-(1-naphthylmethyl)-3-(pyrrolidinocarbonyl)propionyl]-L-histidine azide. The cold azide solution was added dropwise to a solution of 37 mg of methyl (2RS, 3S)-3-amino-2-hydroxy-5-methylhexanoate hydrochloride and 0.053 ml of triethylamine in 1 ml of N,N-dimethylformamide under ice-cooling, and the mixture was stirred for 16 hours. A 5% aqueous sodium bicarbonate solution was added to the reaction mixture, and the mixture was extracted with ethyl acetate. The ethyl acetate layer was washed with a saturated sodium chloride aqueous solution, dried over anhydrous magnesium sulfate, and evaporated under reduced pressure. The residue was purified by preparative silica gel thin layer chromatography (developing solvent: a low layer of chloroform/methanol/water=8/3/1, Rf$_1$=0.52) to obtain 36 mg of methyl (2RS, 3S)-3-{N-[2-(l-naphthylmethyl)-3-(pyrrolidinocarbonyl)propionyl]-L-histidyl}amino-2-hydroxy-5-methylhexanoate as a white powder.

Melting point: 99°–102° C.
Rf$_1$: 0.52.
Rf$_2$: 0.48.
MS: MH+, 606.

EXAMPLE 9

Methyl (2RS, 3S)-3-{N-[2-(1-naphthylmethyl)-3-(dimethylcarbamoyl)propionyl]-L-histidyl}amino-2-hydroxy-5-methylhexanoate To a solution of 100 mg of N-[2-(1-naphthylmethyl)-3-(dimethylcarbamoyl)propionyl]-L-histidine hydrazide in 5 ml of dry N,N-dimethylformamide were added successively 0.15 ml of a dry 5.1N-hydrogen chloride in N,N-dimethylformamide solution and 0.04 ml of isoamyl nitrite at −20° C. with stirring. After disappearance of hydrazide compound, the reaction mixture was cooled to −30° C. and neutralized with 0.11 ml of triethylamine to prepare a solution of N-[2-(1-naphthylmethyl)-3-(dimethylcarbamoyl)propionyl]-L-histidine azide. The cold azide solution was added dropwise to a solution of 50 mg of methyl (2RS, 3S)-3-amino-2-hydroxy-5-methylhexanoate hydrochloride and 0.04 ml of triethylamine in 5 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was dried over anhydrous magnesium sulfate and evaporated reduced pressure. The residue was purified by preparative silica gel thin layer chromatography (developing solvent: a lower layer of chloroform/methanol/- water=8/3/1, $Rf_1$=0.69) to obtain 20 mg of methyl (2RS, 3S)-3-{N-[2-(1-naphthylmethyl)-3-(dimethylcarbamoyl)propionyl]-L-histidyl}amino-2-hydroxy-5-methylhexanoate as a white powder.

Melting point: 117°–121° C.
$Rf_1$: 0.69.
$Rf_2$: 0.68.
MS: MH+, 580.

EXAMPLE 10

Methyl (2RS, 3S)-3-{N-[2-(1-naphthylmethyl)-3-(ethylcarbamoyl)propionyl]-L-histidyl}amino-2-hydroxy-5-methylhexanoate To a suspension of 207 mg of N-[2-(1-naphthylmethyl)-3-(ethylcarbamoyl)propionyl]-L-histidine hydrazide in 3 ml of dry N,N-dimethylformamide were added successively 0.30 ml of a dry 5.1N-hydrogen chloride in N,N-dimethylformamide solution and 0.076 ml of isoamyl nitrite at −20° C. with stirring. After disappearance of hydrazide compound, the reaction mixture was cooled to −30° C. and neutralized with 0.22 ml of triethylamine to prepare a solution of N-[2-(1-naphthylmethyl)-3-(ethylcarbamoyl)propionyl]-L-histidine azide. The cold azide solution was added dropwise to a solution of 100 mg of methyl (2RS, 3S)-3-amino-2-hydroxy-5-methylhexanoate hydrochloride and 0.66 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by silica gel flash column chromatography (eluent chloroform/methanol=15/1, $Rf_1$=0.43) to obtain 77 mg of methyl (2RS, 3S)-3-{N-[2-(1-naphthylmethyl)-3-(ethylcarbamoyl)propionyl]-L-histidyl}amino-2-hydroxy-5-methylhexanoate as a white powder.

Melting point: 103°–108° C.
$Rf_1$: 0.43.
$Rf_2$: 0.32.
MS: MH+, 580.

EXAMPLE 11

Methyl N-[2-(1-naphthylmethyl)-3-(morpholinocarbonyl)propionyl]-L-histidylstatinate Hydrogen chloride was passed into a solution of 100 mg of N-(tert-butyloxycarbonyl)statine (commercially available) in 20 ml of absolute methanol under ice-cooling with stirring, and then the reaction mixture was stirred overnight at room temperature. The reaction mixture was evaporated under reduced pressure to obtain 81 mg of methyl statinate hydrochloride as a colorless viscous oil. [IR (neat): νco 1725 cm$^{-1}$].

To a suspension of 48 mg of N-[2-(1-naphthylmethyl)-3-(morpholinocarbonyl)propionyl]-L-histidine hydrazide in 1 ml of dry N,N-dimethylformamide were added successively 0.065 ml of a dry 5.1N-hydrogen chloride in N,N-dimethylformamide solution and 0.016 ml of isoamyl nitrite at −20° C. with stirring. After disappearance of hydrazide compound, the reaction mixture was cooled to −30° C. and neutralized with 0.046 ml of triethylamine to prepare a solution of N-[2-(1-naphthylmethyl)-3-(morpholinocarbonyl)propionyl]-L-histidine azide. The cold azide solution was added dropwise to a solution of 23 mg of methyl statinate hydrochloride and 0.031 ml of triethylamine in 1 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methanol=5/1, $Rf_2$=0.51) to obtain 5 mg of methyl N-[2-(1-naphthylmethyl)-3-(morpholinocarbonyl)propionyl]-L-histidylstatinate as a white powder.

Melting point: 98°–103° C.
$Rf_1$: 0.54.
$Rf_2$: 0.51.
MS: MH+, 636.

EXAMPLE 12

Isopropyl N-[2-(1-naphthylmethyl)-3-(morphlinocarbonyl)propionyl]-L-histidylstatinate Hydrogen chloride was passed into a solution of 100 mg of N-(tert-butyloxycarbonyl)statine (commercially available) in 5 ml of isopropanol under ice-cooling with stirring, and to the reaction mixture was added 5 ml of dry benzene. The mixture was heated under reflux for 10 minutes while removing water formed during the reaction using a molecular sieve. The reaction mixture was evaporated under reduced pressure to obtain 90 mg of isopropyl statinate hydrochloride as a colorless viscous oil. [IR (neat): νco 1720 cm$^{-1}$].

To a suspension of 94 mg of N-[2-(1-naphthylmethyl)-3-(morpholinocarbonyl)propionyl]-L-histidine hydrazide in 1 ml of dry N,N-dimethylformamide were added successively 0.13 ml of a dry 5.1N-hydrogen chloride in N,N-dimethylformamide solution and 0.031 ml of isoamyl nitrite at −20° C. with stirring. After disappearance of hydrazide compound, the reaction mixture was cooled to −30° C. and neutralized with 0.09 ml of triethylamine to prepare a solution of N-[2-(1-naphthylmethyl)-3-(morpholinocarbonyl)propionyl]L-histidine azide. The cold hydrazide solution was added dropwise to a solution of 50 mg of isopropyl statinate hydrochloride and 0.06 ml of triethylamine in 1 ml of dry N,N-dimethylformamide under ice-cooling, and the mixture was stirred for 16 hours. The reaction mixture was evaporated under reduced pressure, and a 5% aqueous sodium bicarbonate soluiton was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methanol=5/1, $Rf_2$=0.59) to obtain 45 mg of isopropyl N-[2-(1-naphthylmethyl)-3-(morpholinocarbonyl)propionyl]-L-histidylstatinate as a white powder.

Melting point: 94°–98° C.
$Rf_1$: 0.61.
$Rf_2$: 0.59.
MS: MH+, 664.

EXAMPLE 13

N-[2-(1-Naphthylmethyl)-3-(morpholinocarbonyl)propionyl]-L-histidyl-statylisoamylamide To a solution of 100 mg of N-(tert-butyloxycarbonyl)statine (commercially available), and 42 mg of isoamylamine in 3 ml of N,N-dimethylformamide and 3 ml of tetrahydrofuran were added successively 79 mg of 1-hydroxybenzotriazole and 83 mg of dicyclohexylcarbodiimide under ice-cooling with stirring, and the mixture was stirred for 16 hours. Precipitated crystals were filtered off and the filtrate was evaporated under reduced pressure. Ethyl acetate was added to the residue, and the mixture was cooled. Precipitated crystals were filtered off. The tiltrate was washed successively with a 5% aqueous sodium bicarbonate solution and a saturated sodium chloride aqueous solution, dried over anhydrous magnesium sulfate, and evaporated under reduced pressure. The residue was purified by silica gel flash column chromatography (eluent: chloroform/methanol=40/1 by volume) to obtain 132 mg of N-(tert-butyloxycarbonyl)tatylisoamylamide as a colorless viscous oil. [IR (neat): $\nu_{co}$ 1685, 1640 cm$^{-1}$].

To a solution of 130 mg of the amide compound in 10 ml of methanol was added 2 ml of a 2N-hydrochloric acid, and the mixture was stirred for 16 hours at room temperature. The reaction mixture was evaporated under reduced pressure to obtain 57 mg of statylisoamylamide hydrochloride as a white powder. [IR (neat): $\nu_{co}$ 1635 cm$^{-1}$].

To a suspension of 57 mg of N-[2-(1-naphthylmethyl)-3-(morpholinocarbonyl)propionyl]-L-histidine hydrazide in 2 ml of dry N,N-dimethylformamide were added successively 0.076 ml of a dry 5.1-hydrogen chloride in N,N-dimethylformamide solution and 0.019 ml of isoamyl nitrite with stirring at −20° C. After disappearance of hydrazide compound, the reaction mixture was cooled to −30° C. and neutralized with 0.055 ml of triethylamine to prepare a solution of N-[2-(1-naphthylmethyl)-3-(morpholinocarbonyl)propionyl]-L-histidine azide. The cold azide solution was added to a solution of 35 mg of statylisoamylamide hydrochloride and 0.017 ml of triethylamine in 2 ml of dry N,N-dimethylformamide under ice-cooling, and the mixture was stirred for 16 hours. The reaction mixture was evaporated under reduced pressure, and a 5% aqueous sodium bicarbonate solution was added to the residue. The mixture was extracted with ethyl acetate, and the ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methanol=5/1, Rf$_2$=0.48) to obtain 11 mg of N-[2-(1-naphthylmethyl)-3-(morpholinocarbonyl)propionyl]-L-histidylstatylisoamylamide as a white powder.

Melting point: 99°-106° C.
Rf$_1$: 0.69.
Rf$_2$: 0.48.
MS: MH$^+$, 691.

TEST EXAMPLE 1

Human renin-sheep renin substrate reaction system in vitro

To a mixture containing 200 µl of a 125 mM pyrophosphate buffer (pH 7.4), 25 µl of a 20 mM aqueous solution of L-phenylalanyl-L-alanyl-L-prolin as an angiotensin cnverting enzyme inhibitor, 50 µl of semipurified sheep renin substrate (2000 ng angiotensin I/ml), 50 µl of dimethyl sulfoxide solution of an amino acid compound of the present invention and 150 µl of deionized water was added 25 µl of purified human renin (20-30 ng angiotensin I/ml/hr. The mixture was incubated for 15 minutes on a water bath at 37° C., and the reaction mixture was allowed to stand for 5 minutes on a water bath at 100° C. to stop the reaction. After cooling, 200 µl of the solution were taken up and the amount of angiotensin I produced by the addition of renin was determined by radiommunoassay. The inhibitory effect was calculated by the following equation.

As a control, the same procedure as above was carried out by using 50 µl of dimethyl sulfoxide alone in place of the 50 µl of dimethyl sulfoxide solution containing an amino acid compound of the present invention.

The molar concentration which produced a 50% inhibition (IC$_{50}$) was calculated from the inhibition value obtained, and the results are show below.

Inhibition (%) =

$$\frac{\text{Amount of angiotensin I in control} - \text{Amount of angiotensin I in a mixture containing a compound of this invention}}{\text{Amount of angiotensin I in control}} \times 100$$

| Compound | IC$_{50}$ molar concentration |
|---|---|
| Isopropyl (2RS, 3S)—3-{N—[2-(1-naphthylmethyl)-3-(morphalinocarbonyl)propionyl]-L-histidyl}-amino-2-hydroxy-5-methylhexanoate | 2.2 × 10$^{-8}$ M |
| Methyl (2RS, 3S)—3-{N—[2-(1-naphthylmethyl)-3-(morpholinocarbonyl)propionyl]-L-histidyl}-amino-2-hydroxy-5-methylhexanoate | 5.2 × 10$^{-8}$ M |
| Isopropyl (2RS, 3S)—3-{N—[2-(1-naphthylmethyl)-3-(piperidinocarbonyl)propionyl]-L-histidyl}-amino-2-hydroxy-5-methylhaxanoate | 2.8 × 10$^{-8}$ M |
| Methyl (2RS, 3S)—3-{N—[2-(1-naphthylmethyl)-3-(piperidinocarbonyl)propionyl]-L-histidyl}-amino-2-hydroxy-5-methylhexanoate | 4.1 × 10$^{-8}$ M |
| (2RS, 3S)—3-{N—[2-(1-Naphthylmethyl)-3-(piperidinocarbonyl)propionyl]-L-histidyl}amino-2-hydroxy-5-methylhexanoylmethylamide | 6.9 × 10$^{-7}$ M |
| Methyl (2RS, 3S)—3-{N—[2-(1-naphthylmethyl)-3-(pyrolidinocarbonyl)propionyl]-L-histidyl}-amino-2-hydroxy-5-methylhexanoate | 6.9 × 10$^{-8}$ M |
| Methyl (2RS, 3S)—3-{N—[2-(1-naphthylmethyl)-3-(dimethylcarbamoyl)propionyl]-L-histidyl}-amino-2-hydroxy-5-methylhexanoate | 7.8 × 10$^{-8}$ M |
| Methyl (2RS, 3S)—3-{N—[2-(1-naphthylmethyl)-3-(ethylcarbamoyl)propionyl]-L-histidyl}-amino-2-hydroxy-5-methylhexanoate | 6.3 × 10$^{-7}$ M |
| Methyl N—[2-(1-naphthylmethyl)-3-(morpholinocarbonyl)propionyl]-L-histidylstatinate | 2.1 × 10$^{-7}$ M |
| Isopropyl N—[2-(1-naphthylmethyl)-3-(morpholinocarbonyl)propionyl]-L-histidylstatinate | 6.6 × 10$^{-8}$ M |
| N—[2-(1-Naphthylmethyl)-3-(morpholinocarbonyl)propionyl]-L-histidyl-statylisoamylamide | 3.6 × 10$^{-8}$ M |
| (2RS, 3S)—3-{N—[2-(1-Naphthylmethyl)-3-(morpholinocarbonyl)- | 3.4 × 10$^{-7}$ M |

| Compound | IC$_{50}$ molar concentration |
|---|---|
| propionyl]-L-histidyl}amino-2-hydroxy-5-methylhexanoylmethylamide | |
| (2RS, 3S)—{N—[2-(1-Naphthylmethyl)-3-(morpholinocarbonyl)propionyl]-L-histidyl}amino-2-hydroxy-5-methylhexanylisopropylamide | 1.3 × 10$^{-7}$ M |

TEST EXAMPLE 2

Renin inhibitory effect in a human high renin plasma

A mixture of 350 μl of a 0.5 M phosphate buffer containing 14 mM EDTA 2Na and a 0.3% neomycin sulfate, which was adjusted to the pH of 7, 50 μl of a 20 mM an aqueous solution of L-phenylalanyl-L-alanyl-L-prolin as an angiotensin converting enzyme inhibitor and 100 μl of dimethyl sulfoxide solution containing an amino acid compound of the present invention was added to 500 μl of human high renin plasma, and 200 μl of the mixture was incubated at 4° C. in an ice bath, and remaining mixture (800 μl) was incubated for 60 minutes at 37° C. in a water bath. A 200 μl sample was withdrawn from the incubated mixture, chilled immediately in an ice bath, and the amount (A) of angiotensin I produced was determined by radioimmunoassay.

Also, the amount (B) of angiotensin I produced in the incubated mixture at 4° C. in an ice bath was determined by radioimmunoassy.

As a control, the same procedure as above was carried out by using 100 μl of dimethyl sulfoxide alone in place of the 100 μl of dimethyl sulfoxide solution containing an amino acid compound of the present invention.

The renin inhibitory effect in human plasa was calculated by taking the amount of angiotensin I (A) from the amount of angiotensin I (B). The inhibotory effect was calculated by the following equation.

Inhibitory effect (%) =

$$\frac{\text{Amount of angiotensin I in control} - \text{Amount of angiotensin I in a mixture containing a compound of this invention}}{\text{Amount of angiotensin (I) in control}} \times 100$$

The molar concentration which produced 50% inhibition (IC$_{50}$) was calculated from the inhibition value obtained, and the results are shown below.

| Compound | IC$_{50}$ (molar concentration) |
|---|---|
| Isopropyl (2RS, 3S)—3-{N—[2-(1-naphthylmethyl)-3-(morpholinocarbonyl)propionyl]-L-histidyl}-amino-2-hydroxy-5-methylhexanoate | 5.4 × 10$^{-9}$ M |
| Methyl (2RS, 3S)—3-{N—[2-(1-naphthylmethyl)-3-(morpholinocarbonyl)propionyl]-L-histidyl}-amino-2-hydroxy-5-methylhaxanoate | 1.1 × 10$^{-8}$ M |
| Isopropyl (2RS, 3S)—3-{N—[2-(1-naphthylmethyl)-3-(piperidinocarbonyl)propionyl]-L-histidyl}-amino-2-hydroxy-5-methylhaxanoate | 8.8 × 10$^{-8}$ M |
| Methyl (2RS, 3S)—{N—[2-(1-naphthylmethyl)-3-(piperidinocarbonyl)propionyl]-L-histidyl}-amino-2-hydroxy-5-methylhexanoate | 2.4 × 10$^{-8}$ M |
| (2RS, 3S)—3-{N—[2-(1-Naphthylmethyl)-3-(piperidinocarbonyl)propionyl]-L-histidyl}amino-2-hydroxy-5-methylhexanoylmethylamide | 5.2 × 10$^{-6}$ M |
| Methyl (2RS, 3S)—3-{N—[2-(1-naphthylmethyl)-3-(pyrolidinocarbonyl)propionyl]-L-histidyl}-amino-2-hydroxy-5-methylhexanoate | 6.2 × 10$^{-8}$ M |
| Methyl (2RS, 3S)—3-{N—[2-(1-naphthylmethyl)-3-(dimethylcarbamoyl)propionyl]-L-histidyl}amino-2-hydroxy-5-methylhexanoate | 2.5 × 10$^{-8}$ M |
| Methyl N—[2-(1-naphthylmethyl)-3-(morpholinocarbonyl)propionyl]-L-histidylstatinate | 1.5 × 10$^{-7}$ M |

TEST EXAMPLE 3

Hypotensive effect in marmoset

The experiment was carried out by using common marmoset as described in K. G. Hofbauer et al., *Clinical and Experimental hypertension,* Vol. A5, Nos. 7 and 8 (1983), pages 1237–1247.

Furosemide was orally administered three times to common marmoset at 15 mg per kilogram per day every other day to create a high renin state. Blood pressure of consious marmoset was measured 2 days after the last administration of furosemide.

Measurement of blood pressure

Three consious male marmosets marmosets weighing 305–345 g were fixed. Mean blood pressure at tail artery was recorded on pretismograph instrument. The amino acid compound, of the present invention isopropyl (2RS, 3S)-3-{N-[2-(1-naphthylmethyl)-3-(morpholinocarbonylpropionyl]-L-histidyl}amino-2-hydroxy-5-methylhexanoate and administered orally at 30 mg/kg by using a catheter. The results obtained are shown below.

| Time after administration (hours) | Mean blood pressure (mmHg) |
|---|---|
| Control | 103.5 |
| 0.5 | 88.7 |
| 1 | 85.6 |
| 2 | 87.2 |
| 3 | 89.3 |
| 5 | 92.4 |
| 7 | 92.3 |
| 9 | 92.8 |
| 24 | 101.9 |

What is claimed is:

1. An amino acid derivative represented by formula (I)

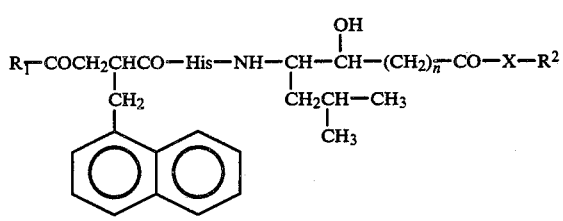

wherein R¹ represents a monoalkylamino group having 1 to 3 carbon atoms, a dialkylamino group having 2 to 6 carbon atoms, or

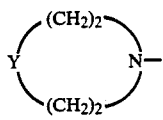

in which Y represents a chemical bond, an oxygen atom or a methylene group, His represents an L-histidyl group, n represents 0 or 1, X represents an oxygen atom or —NH—, R² represents a straight or branched-chain alkyl group having 1 to 7 carbon atoms; or a pharmaceutically acceptable salt thereof.

2. An amino acid derivative as claimed in claim 1 represented by formula:

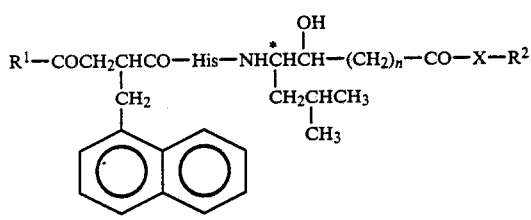

wherein C* represents a carbon atom in the L-configuration, R¹, His, n, X and R² have the same meanings as defined in claim 1, or a pharmaceutically acceptable salts thereof.

3. An amino acid derivative as claimed in claim 2 represented by the formula:

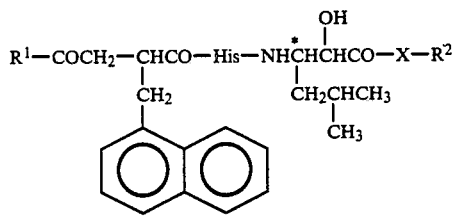

wherein R¹, His, C*, X and R² have the same meanings as defined in claim 2, or a pharmaceutically acceptable salts thereof.

4. An amino acid derivative as claimed in claim 2 represented by formula:

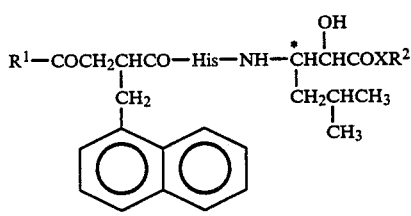

wherein R¹, His, C*, X and R² have the same meanings as defined in claim 2, or a pharmaceutically acceptable salt thereof.

5. The amino acid derivative as claimed in claim 3 represented by formula:

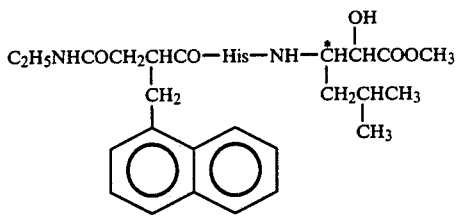

wherein His and C* have the same meanings as defined in claim 3, or a pharmaceutically acceptable salt thereof.

6. The amino acid derivative as claimed in claim 3 represented by formula:

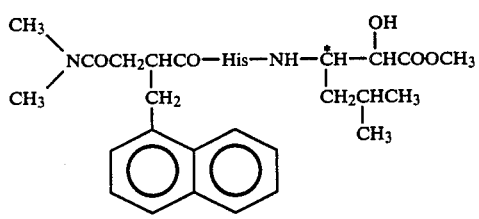

wherein His and C* have the same meanings as defined in claim 3, or a pharmaceutically acceptable salt thereof.

7. The amino acid derivative as claimed in claim 3 represented by formula:

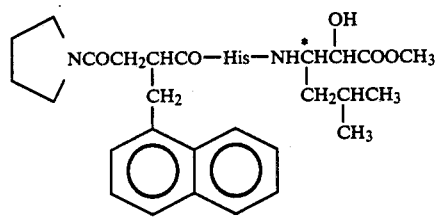

wherein His and C* have the same meanings as defined in claim 3, or a pharmaceutically acceptable salt thereof.

8. The amino acid derivative as claimed in claim 3 represented by formula:

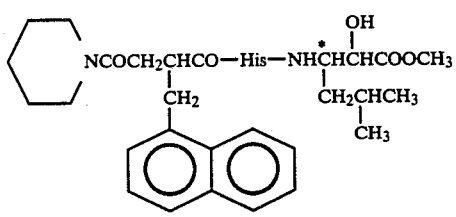

wherein His and C* have the same meanings as defined in claim 3, or a pharmaceutically acceptable salt thereof.

9. The amino acid derivative as claimed in claim 3 represented by formula:

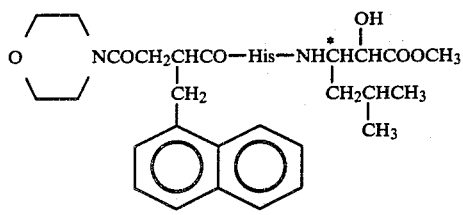

wherein His and C* have the same meanings as defined in claim 3, or a pharmaceutically acceptable salt thereof.

10. The amino acid derivative as claimed in claim 3 represented by formula:

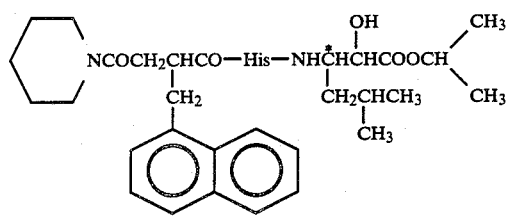

wherein His and C* have the same meanings as defined in claim 3, or a pharmaceutically acceptable salt thereof.

11. The amino acid derivative as claimed in claim 3 represented by formula:

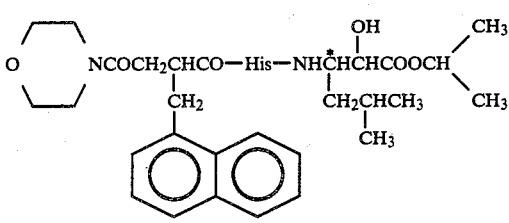

wherein His and C* have the same meanings as defined in claim 3, or a pharmaceutically acceptable salt thereof.

12. The amino acid derivative as claimed in claim 3 represented by formula:

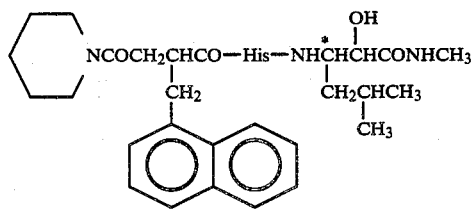

wherein His and C* have the same meanings as defined in claim 3, or a pharmaceutically acceptable salt thereof.

13. The amino acid derivative as claimed in claim 3 represented by formula:

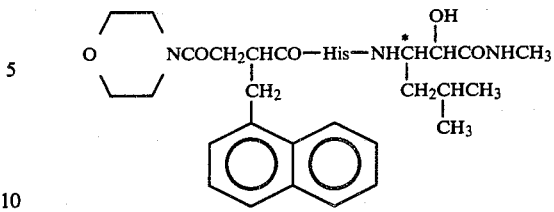

wherein His and C* have the same meanings as defined in claim 3, or a pharmaceutically acceptable salt thereof.

14. The amino acid derivative as claimed in claim 3 represented by formula:

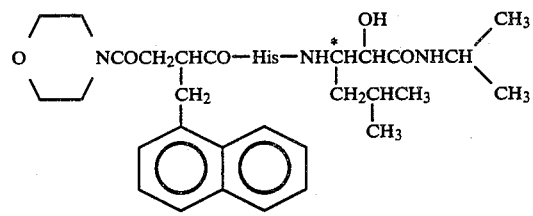

wherein His and C* have the same meanings as defined in claim 3, or a pharmaceutically acceptable salt thereof.

15. The amino acid derivative as claimed in claim 4 represented by formula:

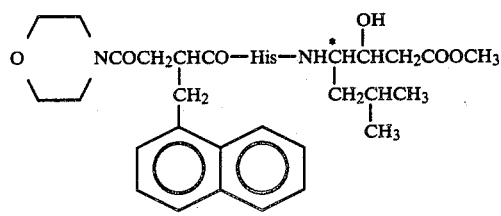

wherein His and C* have the same meanings as defined in claim 4, or a pharmaceutically acceptable salt thereof.

16. The amino acid derivative as claimed in claim 4 represented by formula:

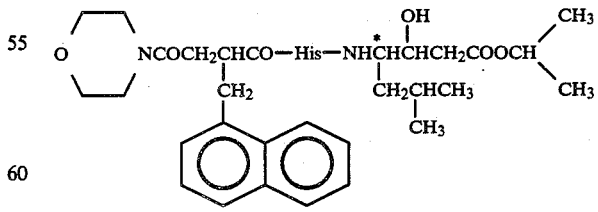

wherein His and C* have the same meanings as defined in claim 4, or a pharmaceutically acceptable salt thereof.

17. The amino acid derivative as claimed in claim 4 represented by formula:

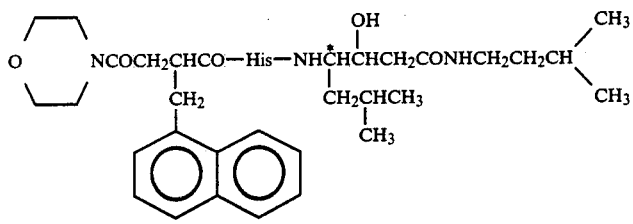
wherein His and C* have the same meanings as claimed in claim 4, or a pharmaceutically acceptable salt thereof.
* * * * *

REEXAMINATION CERTIFICATE (1118th)
United States Patent [19]

Iizuka et al.

[11] B1 4,656,269

[45] Certificate Issued  Aug. 29, 1989

[54] HISTIDINE DERIVITIVES

[75] Inventors: Kinji Iizuka; Tetsuhide Kamijo; Tetsuhiro Kubota, all of Nagano; Kenji Akahane, Tokyo; Hideaki Umeyama, Chiba; Yoshiaki Kiso, Osaka, all of Japan

[73] Assignee: Kissei Pharmaceutical Co., Ltd.

Reexamination Request:
No. 90/001,688, Jan. 10, 1988

Reexamination Certificate for:
Patent No.: 4,656,269
Issued: Apr. 7, 1987
Appl. No.: 852,260
Filed: Apr. 15, 1986

[30] Foreign Application Priority Data

Apr. 15, 1985 [JP] Japan ................... 60-79726

[51] Int. Cl.$^4$ .................. C07D 233/64; C07D 413/12
[52] U.S. Cl. .................................. 544/139; 546/205; 548/336; 548/344

[56]  References Cited

U.S. PATENT DOCUMENTS

| | | |
|---|---|---|
| 4,234,571 | 11/1980 | Nestor et al. |
| 4,548,926 | 10/1985 | Matsueda et al. |
| 4,591,648 | 5/1986 | Jones |
| 4,595,677 | 6/1986 | Riniker et al. |
| 4,666,888 | 5/1987 | Raddatz et al. |
| 4,698,329 | 10/1987 | Matsueda et al. |

FOREIGN PATENT DOCUMENTS

| | | |
|---|---|---|
| 77028 | 4/1983 | European Pat. Off. |
| 77029 | 4/1983 | European Pat. Off. |
| 81783 | 6/1983 | European Pat. Off. |
| 114993 | 8/1984 | European Pat. Off. |
| 173481 | 3/1986 | European Pat. Off. |
| 181110 | 5/1986 | European Pat. Off. |
| 87100424 | 7/1987 | European Pat. Off. |
| 58-39149 | 8/1983 | Japan |
| 60-163899 | 8/1985 | Japan |
| 61-78795 | 4/1986 | Japan |
| 61-152697 | 7/1986 | Japan |
| 61-275256 | 12/1986 | Japan |
| 61-275257 | 12/1986 | Japan |
| 61-275258 | 12/1986 | Japan |
| 61-280459 | 12/1986 | Japan |
| 62-142145 | 6/1987 | Japan |

OTHER PUBLICATIONS

Patent Abstracts of Japan, unexamined applications, C Section, vol. 2, No. 43, Mar. 23, 1978, p. 4928.
Chemical Abstracts 101:23914u (1984).
Chemical Abstracts 95:220299f (1981).
Kokubo et al., "Highly Potent and Specific Inhibitors of Human Renin," Biochemical & Biophysical Research Communictions, vol. 118, pp. 929–933, 1984.
Chemistry Letters, Chem. Soc. Japan No. 7, 1985, pp. 1041–1044.
Abstract of Iizuka et al., presentation at the 106th Annual Meeting of Pharmaceutical Society of Japan, "Design & Synthesis of Renin Inhibitors", published on or about Mar. 10, 1986.
Abstract of Aio et al, presentation at the 50th Annual Meeting of Japanese Circulation Society, published on or about Mar. 1, 1986.
Abstract of Miyazaki et al., presentation at the 50th Annual Scientific Meeting of Japanese Circulation Society, "Hypotensive Effect of a Specific Inhibitor of Human Renin", published on or about 3/1/86.
Abstract of Miyazaki et al., presentation at the 59th General Meeting of the Japanese Pharmacological Society in Apr. 1986, published on or about Mar. 1, 1986.

*Primary Examiner*—R. W. Ramsuer

[57]  ABSTRACT

Novel amino acid derivatives useful as a therapeutic agent are disclosed. These amino acid derivatives and the pharmaceutically acceptable salts thereof have a human renin inhibitory effect when administered orally and are useful for treatment of hypertension, especially renin-associated hypertension.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-17 is confirmed.